United States Patent [19]

Frick et al.

[11] 3,931,413

[45] Jan. 6, 1976

[54] CONTROL OF FUNGI

[75] Inventors: Eric Lionel Frick, Maidstone; Roy Terry Burchill, Bearsted, both of England

[73] Assignee: National Research Development Corporation, London, England

[22] Filed: May 23, 1974

[21] Appl. No.: 472,841

Related U.S. Application Data

[63] Continuation-in-part of Ser. No. 359,505, May 11, 1973, Pat. No. 3,833,736.

[30] Foreign Application Priority Data

June 15, 1972 United Kingdom............... 28026/72

[52] U.S. Cl................................. 424/318; 424/317
[51] Int. Cl.$^2$... A01N 9/00; A01N 9/22; A01N 9/24
[58] Field of Search ............ 424/311, 312, 317, 318

[56] References Cited
UNITED STATES PATENTS

| | | | |
|---|---|---|---|
| 1,589,866 | 6/1926 | Siegler et al. | 424/318 |
| 2,030,093 | 2/1936 | Bousquet et al. | 424/311 |
| 2,576,987 | 12/1951 | Wyman | 424/318 |
| 3,717,706 | 2/1973 | McGovern et al. | 424/311 |
| 3,849,558 | 11/1974 | Nakamura | 424/312 |

OTHER PUBLICATIONS

"Fungicides and their Actions," J. G. Horsfall, 1945, Chronica Botanica Co., pp. 148–149.
"Chemistry of the Pesticides," D. E. Frear, 3rd ed. D. Van Nostrand Co., Inc. N.Y. pp. 293–294, 1955.

*Primary Examiner*—Albert T. Meyers
*Assistant Examiner*—D. W. Robinson
*Attorney, Agent, or Firm*—Oblon, Fisher, Spivak, McClelland & Maier

[57] ABSTRACT

A method for the control of fungi which have an overwintering phase inside the buds of a plant or on other parts thereof comprises treating a plant selected from the group consisting of food crop and ornamental plants whilst the plant or at least the buds thereof are dormant or in a state of near dormancy with a fungicidal composition comprising as an active component a compound selected from the group consisting of medium chain aliphatic acids.

18 Claims, No Drawings

CONTROL OF FUNGI

This application is a continuation-in-part derived from our co-pending application Ser. No. 359,505, filed May 11, 1973, now U.S. Pat. No. 3,833,736.

BACKGROUND OF THE INVENTION

1. Field of the Invention

This invention relates to the control of fungi.

2. Description of the Prior Art

Fungi which overwinter on a plant, especially inside the buds of the plant, are difficult to control as the fungus is already present on the plant in an active form at bud burst. Thus, for example, the fungus *Podosphaera leucotricha* (Ell. and Ev.) Salm. presents a major problem to commercial apple growers but, although the fungus has been known as the cause of a disease of apple and pear trees for nearly a century, none of the various methods which have been used in an attempt to combat the fungus have been successful in effecting more than a limited degree of control of the disease. A method has now been discovered employing certain fatty acids and fatty acid derivatives which has been found to give far better control of *Podosphaera leucotricha* and like fungi than it has previously been possible to achieve.

It is known that many of the compounds used in the method of the present invention exert a fungicidal action against certain fungi as disclosed, for example, in the following papers: "Effects of vapours of aromatic chemicals on fungi," Journal of Pharmaceutical Sciences, 1961, 50, 665 – 668; "Antifungal properties of methyl esters of fatty acids and 2-fluoro fatty acids," Contributions from Boyce Thompson Institute, 1970, 24, 245 – 247; and "Action of odiferous organic chemicals and essential oils in wood-destroying fungi," Plant Disease Reporter, 1960, 44, 789 – 792. However, in the above references these compounds are shown to be wholly or partially inactive against a variety of fungi tested. The present discovery, therefore, that fungi which overwinter inside the buds of a plant or on other parts thereof, e.g. *Podosphaera leucotricha* and *Venturia inaequalis*, can now be controlled by these same compounds is clearly an unexpected and unpredictable result, which is even more unpredictable in view of the fact that all previous attempts to control these fungi have failed to a satisfactory degree.

It is also known that many of the compounds may be used on plants, including apples, as chemical pruning agents as disclosed, for example, in the papers "Plant growth inhibition by some fatty acids and their analogues," Nature, 1964, 202, 511 – 512; "Chemical pruning of plants," Science, 1966, 153, 1382 – 1383; and "Modern chemical pruning of plants," Florist and Nursery Exchange, Apr. 14, 1970, 6 – 13; and in the specifications of U.S. Pat. Nos. 3,326,664; 3,340,040; 3,438,765; and 3,620,712. However, the use of these compounds as chemical pruning agents is effective only on rapidly growing plants and it is specifically stated in these publications that dormant or resting plants exhibit no selective response to these compounds, so that no one would expect these compounds to have an important application out of the growing season.

SUMMARY OF THE INVENTION

According to the present invention a method for the control of fungi which have an overwintering phase inside the buds of a plant or on other parts thereof comprises treating a plant selected from the group consisting of food crop and ornamental plants whilst the plant or at least the buds thereof are dormant or in a state of near dormancy with a fungicidal composition comprising as an active component a compound selected from the group consisting of medium chain aliphatic acids and alcohols, and esters of medium and short chain aliphatic acids.

DETAILED DESCRIPTION OF THE PREFERRED EMBODIMENTS

Although the compounds used in the method of the present invention may be saturated or unsaturated and straight or branched chain, saturated straight chain compounds are of rather more interest, e.g. those compounds consisting of a linear alkane substituted at one end by a hydroxy group, carboxy group or carbalkoxy group, in which the alkyl group is straight chain. It will be appreciated that when the compound used in the method of the present invention is an acid the acid may, if desired, be in the form of a salt. Reference herein to the use of an acid is, therefore, to be construed as extending to the use of salts of that acid. Salts of particular interest are those having an enhanced solubility as compared with the acid itself. Examples of salts are the ammonium or alkali metal salts and especially the sodium salt.

Medium chain acids and alcohols of interest are those containing from about six to about eighteen carbon atoms. Compounds of especial interest are those containing from six or eight to 12 or 14 carbon atoms, particularly those containing the even number eight and 10 carbon chains and those containing the odd number seven and nine carbon chains.

Specific examples of acids and alcohols which may be used in the method of the present invention include hexanoic acid, heptanoic acid, octanoic acid, nonanoic acid, decanoic acid, undecanoic acid, dodecanoic acid, tetradecanoic acid, perlagonic acid, hexan-1-ol, heptan-1-ol, octan-1-ol, nonan-1-ol, decan-1-ol, dodecan-1-ol, tetradecan-1-ol, 2-ethylhexan-1-ol, 3,5,5-trimethylhexan-1-ol, 4,6-dimethylheptan-2-ol, 2,4,6-trimethylheptan-1-ol, and 2-methyloctan-1-ol. Specific examples of longer chain compounds which may be used, but which are generally of rather lesser interest, include hexadecanoic acid, octadecanoic acid, oleic acid, linoleic acid, hexadecan-1-ol and octadecan-1-ol.

Esters of interest are those containing from five to 24 carbon atoms having from one to 18 carbon atoms in the alcohol moiety and from one to 18 carbon atoms in the acid moiety. Compounds of especial interest are those containing up to 14 or 18 carbon atoms with at least one carbon atom in each moiety, for example those containing from six to 10 or 12 carbon atoms, particularly those containing at least seven or eight carbon atoms. One group of preferred compounds comprises those containing one, two or three carbon atoms in the alcohol moiety and from six or eight to 12 or 14 carbon atoms in the acid moiety, particularly the methyl esters of the even number eight and 10 carbon chain acids and of the odd number nine and 11 carbon chain acids, and the ethyl esters of the even number six and eight and odd number seven carbon chain acids. Another group of preferred compounds comprises those containing from six or eight to 12 or 14 carbon atoms in the alcohol moiety and from one to four carbon atoms in the acid moiety, particularly the octyl and as possible consistent with effective control of the fungus is preferred in order to minimise any phytotoxic effect of the composition. Whilst treatment of the buds is most important in the case of bud-overwintering fungi, it is in practice usually simplest to apply the composition to the whole of the plant. In the case of apples and pears, for example, one treatment of the whole plant can provide control of not only *Podosphaera leucotricha* but also *Venturia inaequalis* and *Venturia pirina*.

In order to ensure thorough wetting, the compounds can be applied in the form of a composition comprising an effective proportion of a suitable surface active agent. The alcohols have the advantage of themselves possessing wetting properties. Whilst a wide variety of surface active agents may be used, anionic and particularly non-ionic materials are preferred, if desired in admixture together and/or with a minor proportion of a cationic surface active agent. Examples of types of surface active agents which may be used are:

1. The polyethylene oxide condensates of alkylphenols e.g. the condensation products of alkylphenols or dialkylphenols wherein the alkyl group contains from about six to about 12 carbon atoms in either branched chain or particularly straight chain configuration, with ethylene oxide, the said ethylene oxide being present in amounts equal to about 5 to about 25 moles of ethylene oxide per mole of alkylphenol.

2. The ammonia, monoethanol and diethanol amides of fatty acids having an acyl chain of from about eight to about 18 carbon atoms. These acyl chains are normally derived from naturally occurring glycerides (e.g. coconut oil, palm oil, soybean oil and tallow) but can be derived synthetically (e.g. by the oxidation of petroleum, or by hydrogenation of carbon monoxide by the Fischer-Tropsch process).

3. Fatty acid esters of polyoxyethylene sorbitan and sorbitol containing from about three to about 80 oxyethylene units per molecule and containing fatty acid groups having from about 8 to about 18 carbon atoms.

4. The condensation product of aliphatic alcohols having from about eight to about 18 carbon atoms, in either straight chain or branched chain configuration, with ethylene oxide, the said ethylene oxide being present in amounts equal to about 30 to about 60 moles of ethylene oxide per mole of alcohol.

5. Anionic surfactants which are the phosphate esters of polyoxyethylenated alkylphenols, such as nonyl phenol, and aliphatic alcohols, such as tridecyl alcohol. These surfactants have the general formulae

and
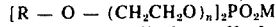

wherein R is an alkyl or alkyl phenyl group containing from about eight to about 20 carbon atoms, wherein $n$ is a number from about 3 to about 40, and wherein M is an alkali metal, e.g. sodium or potassium, and mixtures thereof.

Of these the fatty acid esters of polyoxyethylene sorbitol and especially polyoxyethylene sorbitan are of particular interest. Suitable fatty acids useful in forming the esters including octanoic, nonanoic, decanoic, undecanoic, dodecanoic, tridecanoic, tetradecanoic, pentadecanoic, hexadecanoic, heptadecanoic and octadecanoic acids or mixtures thereof. For ease of formulation the ester preferably contains not more than about 30 oxyethylene units, for example from three or five to about ten or from about ten to about 30 units.

Examples of preferred surface active agents of this type are particularly the mono-dodecanoate ester of polyethoxylated sorbitan containing an average of about 20 oxyethylene units per molecule, but also the mono-oleate and mono-octadecanoate esters of polyethoxylated sorbitan containing an average of about 20 oxyethylene moieties per molecule and the mono-dodecanoate ester of polyethoxylated sorbitan containing an average of about five oxyethylene units per molecule. Examples of other surface active agents include the following condensation products: 1 mole of sorbitan mono-dodecanoate with 4 moles of ethylene oxide, 1 mole of sorbitan mono-octadecanoate with 4 moles of ethylene oxide, and 1 mole of sorbitan mono-oleate with 5 moles of ethylene oxide.

The use of a suitable surface active agent can often give significantly improved results aiding particularly in achieving a balance between fungicidal and general phytotoxic actions. This is particularly true in the case of the acids where the use of an increased amount of surface active agent can lead to a marked reduction in phytotoxicity. The best form of surface active agent for use in any particular situation may readily be ascertained by a series of simple tests on small specimens in the greenhouse (as described in the Examples) these being more readily carried out and giving a good indication of the requirements for the outdoor treatment of the plant.

The proportion of surface active agent used can vary widely according to the circumstances. Thus although in some instances a small proportion by weight of from about 0.01 to about 0.05% may be used, in other instances it may be desirable to increase the proportion signficantly, for example to give for one part by weight of compound(s) a portion of about 0.2, 0.3, 0.5 or one part of surface active agent. Even larger proportions of surface active agent than this may be used with advantage in the case of the acids.

In addition to surface active agents other additives may be included, most particularly emulsifiers (although many of the surface active agents themselves act as emulsifiers), for example compounds such as Triton X100.

The invention is illustrated by the following Examples.

EXAMPLE 1

Effect of fungicidal composition on *P.leucotricha* on apples a. Six year old heavily mildewed apple trees (clone M3) are sprayed high volume by hand lance at different times with fungidical compositions containing either an alkanol mixture comprising: 0.5% hexan-1-ol, 42% octan-1-ol, 56% decan-1-ol, and 1.5% dodecan-1-ol, or a methyl alkanoate mixture comprising 4% methyl hexanoate, 56% methyl octanoate, 38% methyl decanoate, and 2% methyl dodecanoate, (the % being w/w in each case), in combination with the surface active agent Tween 80 [polyoxyethylene (20) sorbitan mono-oleate].

The exact conditions of treatment are shown in Table 1, both autumn applications being made whilst the leaves are still green and the spring application just as the buds begin to swell in the first stage of bud burst. Assessments of the effect of the treatment are made in April/May when primary mildew infections will be clearly visible. The total number of buds, and whether each is healthy, mildewed or dead, is recorded on ten 1-year old shoots per tree. All the primary infections on each tree are also counted.

Results typical of those obtained are shown in Tables 1 and 2. It will be seen that the early autumn sprays give better mildew control than the later ones, but are more damaging to the upper part of the shoots, particularly in the case of the alkanol mixture. Typically it is found that the additional application in March initially delays bud break but that growth quickly returns to normal, whilst with the other treatments shoot growth is unaffected and if the terminal bud is killed or damaged a single shoot quickly replaces it.

Table 1:

Effect of treatment on overall reduction of primary mildew

| | Details of Treatment[1] | Number of trees | Total mildewed buds | Average mildewed buds per tree | % Mildew reduction |
|---|---|---|---|---|---|
| 1. | 5% methyl alkanoates in early October | 8 | 13 | 1.6 | 98.7 |
| 2. | 5% alkanols in early October | 8 | 11 | 1.4 | 98.9 |
| 3. | 5% methyl alkanoates in early November | 9 | 112 | 12.3 | 90.3 |
| 4. | 5% alkanols in early November | 9 | 88 | 9.8 | 92.3 |
| 5. | 5% methyl alkanoates in early October followed by 2.5% methyl alkanoates in late March | 8 | 1 | 0.1 | 99.9 |
| 6. | Unsprayed control | 20 | 2,535 | 126.7 | — |

[1] All percentages are w/v

TABLE 2:

Effect of treatment on primary bud infections

| Treatment | Number of trees | Total number of buds | % Dead | % Healthy | % Mildewed |
|---|---|---|---|---|---|
| 1 | 8 | 2,138 | 15.7 | 84.2 | 0.1 |
| 2 | 8 | 2,184 | 17.1 | 82.7 | 0.2 |
| 3 | 9 | 2,278 | 6.3 | 91.3 | 2.4 |
| 4 | 9 | 2,456 | 5.4 | 93.8 | 0.8 |
| 5 | 8 | 2,132 | 14.5 | 85.5 | 0.0 |
| 6 | 20 | 5,315 | 6.4 | 76.7 | 16.9 | b. A range of acids, alcohols and esters comprising heptan-1-ol, octan-1-ol, nonan-1-ol, decan-1-ol, octan-1-ol/decan-1-ol mixtures, 3,5,5-trimethylhexan-1-ol, methyl octanoate, methyl decanoate, methyl octanoate/methyl decanoate mixtures, decanoic acid, ethyl octanoate and n-hexyl acetate, are used substantially as described under (a) for the control of *P. leucotricha* on apples. Typically each of these compounds effects control of the fungus but with varying levels of phytotoxic effect.

c. Tests of fungicidal compositions are carried out in the greenhouse to study the relative activity of various compounds. The following active ingredients are used: the alkanol and methyl alkanoate mixtures described under (a) at 3 and 5% (w/v) concentration and heptan-1-ol, octan-1-ol, nonan-1-ol, decan-1-ol, 3,5,5-trimethylhexan-1-ol, methyl octanoate, methyl decanoate, octanoic acid and decanoic acid at 5% (w/v) concentration. In addition compositions contain by volume 0.5% acetone, 0.015% Triton X100 and 0.05 Tween 80 in water. Heavily mildewed potted apple rootstocks are sprayed once during the dormant season with the composition and assessments of the effect of the treatment are made in April/May when primary mildew infections will be clearly visible.

Typically the results are as follows. The treatments with 3% alkanol or methyl alkanoate mixtures are less damaging than those with 5% mixtures but give somewhat less effective control of the primary mildew. Methyl decanoate is more damaging than methyl octanoate but gives more effective control, but decanoic acid is less damaging than octanoic acid and gives more effective primary mildew control. Among the alcohols the following relative levels of damage are found: heptan-1-ol<nonan-1-ol~3,5,5-trimethylhexan-1-ol<octan-1-ol<decan-1-ol and of primary mildew control 3,5,5-trimethylhexan-1-ol>nonan-1-ol>decan-1-ol>octan-1-ol>heptan-1-ol.

d. Tests of fungicidal compositions are carried out in the greenhouse with compositions containing by volume 5% octanoic, decanoic acid or undecanoic acid, 0.5% acetone, 0.015% Triton X100 (a condensate between one mole of octyl phenol and 9 to 10 moles of ethylene oxide) and 0.05% Tween 80 in water. Heavily mildewed potted apple plants (clone M3) are sprayed with the composition once during the dormant season and assessments of the effect of the treatment are made in April/May when primary mildew infections will be clearly visible.

Typical results with decanoic acid are total buds — 104; % of dead buds — 55; % of unbroken (dormant) buds — 22; % of broken buds — 23; % of broken buds with primary mildew — 0. Typical results with undecanoic acid indicate similar levels of damage and mildew control whilst those with octanoic acid indicate slightly more damage and not quite such effective mildew control as compared with decanoic acid.

In variations of the tests the Tween 80 surface active agent is replaced by Tween 20 [polyoxyethylene (20) sorbitan monododecanoate] or a mixture of equal parts by volume of Tween 20 and Tween 80, substantially similar results typically being obtained.

e. In tests similar to those described in (d) the 0.05% Tween 80 is replaced by 0.5% or 2.0% Tween 80. Typically a reduction in phytotoxicity is observed whilst the mildew control is substantially similar.

f. Heavily mildewed apple trees (clone M3) are sprayed high volume by hand lance during the autumn whilst the buds are dormant but before leaf fall with a fungicidal composition containing 5% w/v decanoic acid in combination with the surface active agent Tween 80. Assessment of the effect of the treatment is made in the spring when primary mildew infections will be clearly visible. Typically a similar level of control of primary mildew is obtained to that achieved under similar conditions with the 5% alkanol mixture described under (a), whilst the level of damage is of a similar order or slightly increased in comparison.

EXAMPLE 2

Effect of fungicidal compositions on *V. inaequalis* on apples

Six year old apple trees (clone M3) infected with apple scab (*Venturia inaequalis*) are sprayed high volume by hand lance during the autumn whilst the leaves are still green with fungicidal compositions containing either an alkanol mixture comprising 0.5% hexan-1-ol, 42% octan-1-ol, 56% decan-1-ol and 1.5% dodecan-1-ol, or a methyl alkanoate mixture comprising 4% methyl hexanoate, 56% methyl octanoate, 38% methyl decanoate and 2% methyl dodecanoate (the % being w/w in each case), in combination with the surface active agent Tween 80.

Varying conditions of treatment are used as shown in Table 3, and assessment of the effect of the treatment are made in the spring by measurement of the Ascospore concentrations released. Results typical of those obtained are shown in Table 3.

Table 3:

Effect of treatments on Ascospore concentrations of *Venturia inaequalis*

| | Details of treatment[1] | Ascospore concentration $ml^{-1}$ |
|---|---|---|
| 1. | 10% methyl alkanoates | 0 |
| 2. | 5% methyl alkanoates | 0 |
| 3. | 2.5% methyl alkanoates | 0 |
| 4. | 10% alkanols | 0 |
| 5. | 5% alkanols | 0 |
| 6. | 2.5% alkanols | 0 |
| 7. | Control sprayed with water | 618,000 |

[1]All percentages are w/v

We claim:

1. A method for the treatment of plants in order to inhibit infection caused by a fungus which is capable of overwintering in the bud of the plant said fungus selected from the group consisting of *Venturia inaequalis*, *Venturia pirina*, *Podosphaera leucotricha*, *Sphaerotheca pannosa* var. *Persicae*, *Uncinula necator* and *Taphrina deformans*, which consists essentially of applying a fungidical amount of an aliphatic acid containing six to 18 carbon atoms to said buds of the plant during the period of dormancy of said buds.

2. A method according to claim 1, wherein the plant is selected from the group consisting of an apple tree, a pear tree, a peach tree, a rose bush and a grape vine.

3. A method for the treatment of plants in order to inhibit infection caused by a fungus of the type which is capable of overwintering in the bud of the plant, which fungus infection is caused by a fungus selected from the group consisting of *Venturia inaequalis*, *Venturia pirina* and *Podosphaera leucotricha*, which consists essentially of applying a fungicidal amount of an aliphatic acid containing six to 18 carbon atoms to the buds of the plant during the period of dormancy of said buds.

4. A method according to claim 3, wherein the plant is selected from the group consisting of an apple tree and a pear tree.

5. A method according to claim 3, wherein said fungus infection is caused by *Podosphaera leucotricha* and the plant is an apple.

6. A method according to claim 1, wherein said compound is selected from the group consisting of an aliphatic acid containing from six to 12 carbon atoms.

7. A method according to claim 6 wherein said compound is selected from the group consisting of octanoic, decanoic and undecanoic acid.

8. A method according to claim 6, wherein said compound is decanoic acid.

9. A method according to claim 6, wherein said compound is undecanoic acid.

10. A method according to claim 1, wherein the plant is treated during the period of dormancy of the buds before leaf fall.

11. A method according to claim 1, wherein the compound is applied to the plant in the form of a composition containing from 1 to 6% (w/v) of the compound in a diluent or carrier.

12. A method according to claim 11, wherein said composition contains from 3 to 5% (w/v) of the compound in a diluent or carrier.

13. A method according to claim 1, wherein the compound is applied to the plant as an aqueous composition at high volume.

14. A method according to claim 1, wherein the aliphatic acid is applied to the plant in the form of a composition containing a surface active agent.

15. A method according to claim 14, wherein said surface active agent is non-ionic or anionic.

16. A method according to claim 15, wherein said surface active agent is a fatty acid ester of a polyoxyethylene sorbitan containing from about three to about 80 oxyethylene units per molecule and wherein the fatty acid group has from about eight to about 18 carbon atoms.

17. A method according to claim 16, wherein said surface active agent is selected from the group consisting of a dodecanoate ester of polyethoxylated sorbitan containing an average of 20 oxyethylene units per molecule, an oleate ester of polyethoxylated sorbitan containing an average of 20 oxyethylene units per molecule, and a dodecanoate ester of polyethoxylated sorbitan containing an average of about five oxyethylene units per molecule.

18. A method according to claim 15, wherein said surface active agent is a polyethylene oxide condensate of an alkyl phenol wherein the alkyl group contains from six to 12 carbon atoms, and wherein said ethylene oxide is present in an amount of from 5 to 25 moles of ethylene oxide per mole of alkyl phenol.

* * * * *